United States Patent
Sharma et al.

(10) Patent No.: US 11,830,606 B2
(45) Date of Patent: Nov. 28, 2023

(54) RISK PREDICTION FOR COVID-19 PATIENT MANAGEMENT

(71) Applicant: Siemens Healthcare GmbH, Erlangen (DE)

(72) Inventors: Puneet Sharma, Princeton Junction, NJ (US); Ingo Schmuecking, Yardley, PA (US); Sasa Grbic, Plainsboro, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 330 days.

(21) Appl. No.: 16/891,309

(22) Filed: Jun. 3, 2020

(65) Prior Publication Data
US 2021/0330269 A1 Oct. 28, 2021

Related U.S. Application Data

(60) Provisional application No. 63/016,324, filed on Apr. 28, 2020.

(51) Int. Cl.
*G16H 30/40* (2018.01)
*G16H 70/60* (2018.01)
(Continued)

(52) U.S. Cl.
CPC .......... *G16H 30/40* (2018.01); *A61B 5/7267* (2013.01); *A61B 5/7275* (2013.01);
(Continued)

(58) Field of Classification Search
CPC ... A61B 5/7275; A61B 5/7267; A61B 6/5217; A61B 8/5223; A61B 5/055; A61B 6/032;
(Continued)

(56) References Cited

U.S. PATENT DOCUMENTS

| | | | |
|---|---|---|---|
| 2008/0233576 A1* | 9/2008 | Weston | G16B 25/10 707/999.005 |
| 2019/0239843 A1* | 8/2019 | Bregman-Amitai | A61B 6/032 |

(Continued)

FOREIGN PATENT DOCUMENTS

| | | |
|---|---|---|
| CN | 107220506 A | 9/2017 |
| EP | 3576100 A1 | 12/2019 |

OTHER PUBLICATIONS

Guan et al., Clinical Characteristics of Coronavirus Disease 2019 in China, Feb. 28, 2020, The New England Journal of Medicine, pp. 1-13 (Year: 2020).*

(Continued)

*Primary Examiner* — Robert A Sorey
*Assistant Examiner* — Kimberly A. Sass

(57) ABSTRACT

Systems and methods for predicting risk for a medical event associated with evaluating or treating a patient for a disease are provided. Input medical imaging data and patient data of a patient are received. The input medical imaging data includes abnormality patterns associated with a disease. Imaging features are extracted from the input medical imaging data using a trained machine learning based feature extraction network. One or more of the extracted imaging features are normalized. The one or more normalized extracted imaging features and the patient data are encoded into features using a trained machine learning based encoder network. Risk for a medical event associated with evaluating or treating the patient for the disease is predicted based on the encoded features.

20 Claims, 7 Drawing Sheets

(51) Int. Cl.

| | | |
|---|---|---|
| *G16H 50/50* | (2018.01) | |
| *G16H 30/20* | (2018.01) | |
| *G16H 50/30* | (2018.01) | |
| *G16H 50/70* | (2018.01) | |
| *G16H 50/20* | (2018.01) | |
| *G16H 70/20* | (2018.01) | |
| *A61B 5/00* | (2006.01) | |
| *A61B 6/00* | (2006.01) | |
| *A61B 8/08* | (2006.01) | |
| *G06T 7/00* | (2017.01) | |
| *A61B 5/055* | (2006.01) | |
| *A61B 6/03* | (2006.01) | |

(52) U.S. Cl.
CPC .......... *A61B 6/5217* (2013.01); *A61B 8/5223* (2013.01); *G06T 7/0012* (2013.01); *G16H 30/20* (2018.01); *G16H 50/20* (2018.01); *G16H 50/30* (2018.01); *G16H 50/50* (2018.01); *G16H 50/70* (2018.01); *G16H 70/20* (2018.01); *G16H 70/60* (2018.01); *A61B 5/055* (2013.01); *A61B 6/032* (2013.01); *A61B 8/08* (2013.01); *G06T 2207/30061* (2013.01)

(58) Field of Classification Search
CPC .................... A61B 8/08; G06T 7/0012; G06T 2207/30061; G06V 30/194; G16H 30/20; G16H 30/40; G16H 50/20; G16H 50/30; G16H 50/50; G16H 50/70; G16H 70/20; G16H 70/60; G06N 20/00
See application file for complete search history.

(56) References Cited

U.S. PATENT DOCUMENTS

| | | | | |
|---|---|---|---|---|
| 2019/0371450 | A1* | 12/2019 | Lou | ........................ G16H 20/40 |
| 2020/0069973 | A1 | 3/2020 | Lou et al. | |
| 2020/0211694 | A1* | 7/2020 | Nye | ........................ G06T 7/0016 |
| 2021/0042916 | A1* | 2/2021 | Zhang | ..................... A61B 6/50 |

OTHER PUBLICATIONS

Extended European Search Report (EESR) dated Sep. 24, 2021 in corresponding European patent application No. 21170708.8.

Xiaolong, Qi et al: "Conclusions"; medRxiv; Mar. 3, 2020 (Mar. 3, 2020).

Chassagnon, Guillaume et al: "AI-Driven CT-based quantification, staging and short-term outcome prediction of COVID-19 pneumonia"; arxiv.org, Cornell University Library, 201 Olin Library Cornel University Ithaca, NY 14853; Apr. 20, 2020 (Apr. 20, 2020).

Gozes, Ophier et al: "Rapid AI Development Cycle for the Coronavirus (COVID-19) Pandemic: Initial Results for Automated Detection & Patient Monitoring using Deep Learning CT Image Analysis"; (2020); arxiv.org; Cornell University Library; pp. 1-19.

Wu, Yu-Huan et al: "JSC: An Explainable COVID-19 Diagnosis System by Joint Classification and Segmentation"; arxiv.org, Cornell University Library, 201 Olin Library Cornel University Ithaca, NY 14853; Apr. 15, 2020 (Apr. 15, 2020).

Wynants et al., "Prediction models for diagnosis and prognosis of covid-19 infection: systematic review and critical appraisal", The BMJ, BMJ2020;369:m1328, Apr. 2020, pp. 1-11.

Jones et al., "The Sequential Organ Failure Assessment score for predicting outcome in patients with severe sepsis and evidence of hypoperfusion at the time of emergency department presentation", Crit Care Med., May 2009, vol. 37, No. 5, pp. 1-13.

Guo et al., "Clinical Features Predicting Mortality Risk in Patients With Viral Pneumonia: The MuLBSTA Score", Frontiers in Microbiology, Dec. 2019, vol. 10, No. 2752, pp. 1-10.

Shi et al., "Association of Cardiac Injury With Mortality in Hospitalized Patients With COVID-19 in Wuhan, China", JAMA Cardiology, published online Mar. 25, 2020, https://doi:10.1001/jamacardio.2020.0950, pp. E1-E8.

Guo et al., "Cardiovascular Implications of Fatal Outcomes of Patients With Coronavirus Disease 2019 (COVID-19)", JAMA Cardiology, published online Mar. 27, 2020, https://doi:10.1001/jamacardio.2020.1017, pp. E1-E8.

Rotzinger et al., "Pulmonary Embolism in Patients with COVID-19: Time to Change the Paradigm of Computed Tomography", Thrombosis Research, 2020, vol. 190, pp. 58-59.

Cui et al., "Prevalence of Venous Thromboembolism in Patients with Severe Novel Coronavirus Pneumonia", J Thromb Haemost, Apr. 2020, https://doi.org/10.1111/jth.14830, pp. 1-4.

Jiang Zhengfeng et al: "Intelligent assisted diagnosis of COVID-19 based on CT images"; Apr. 20, 2020.

Yu Long; et al: "Clinical characteristics of pneumonia caused by novel coronavirus infection in the elderly"; Apr. 25, 2020 (with English abstract).

Wang Zhi; et al:"Research on risk prediction model of nosocomial infection of cerebrovascular diseases based on BP neural network"; Apr. 30, 2017.

* cited by examiner

RISK PREDICTION FOR COVID-19 PATIENT MANAGEMENT

CROSS-REFERENCE TO RELATED APPLICATIONS

This application claims the benefit of U.S. Provisional Application No. 63/016,324, filed Apr. 28, 2020, the disclosure of which is incorporated herein by reference in its entirety.

TECHNICAL FIELD

The present invention relates generally to risk prediction for patient management, and in particular to comprehensive risk prediction for patient management of patients suspected of, or confirmed as, having COVID-19 (coronavirus disease 2019).

BACKGROUND

COVID-19 (coronavirus disease 2019) is an infectious disease caused by the severe-acute respiratory symptom coronavirus 2 (SARS-Cov2). Common symptoms of COVID-19 include fever, cough, and difficulty breathing. In the majority of cases, patients infected with COVID-19 experience mild to moderate symptoms that do not require hospitalization. However, in severe cases, COVID-19 can cause pneumonia, severe acute respiratory syndrome, multiple organ failure, and death.

In the current clinical workflow, diagnostic imaging is typically performed on patients suspected of having COVID-19 to visualize the extent and severity of COVID-19 in the lungs and other organs. Such imaging comprises a wealth of quantitative and qualitative information. However, extraction of all of the information from the imaging is challenging. Additionally, visual assessment of the imaging by a radiologist to determine the qualitative information is subjective and often narrowly focused. Accordingly, such quantitative and qualitative information from the imaging data is currently underutilized for patient management of patients suspected of, or confirmed as, having COVID-19.

BRIEF SUMMARY OF THE INVENTION

In accordance with one or more embodiments, systems and methods for predicting risk for a medical event associated with evaluating or treating a patient for a disease are provided. Input medical imaging data and patient data of a patient are received. The input medical imaging data includes abnormality patterns associated with a disease. Imaging features are extracted from the input medical imaging data using a trained machine learning based feature extraction network. One or more of the extracted imaging features are normalized. The one or more normalized extracted imaging features and the patient data are encoded into features using a trained machine learning based encoder network. Risk for a medical event associated with evaluating or treating the patient for the disease is predicted based on the encoded features.

In one embodiment, the disease is COVID-19 (coronavirus disease 2019) and the abnormality patterns include at least one of GGO (ground glass opacity), consolidation, and crazy-paving pattern. In another embodiment, the disease is a pneumonia.

In one embodiment, normalizing the one or more extracted imaging features includes normalizing the one or more extracted imaging features with respect to other ones of the extracted imaging features or temporally normalizing the one or more extracted imaging features with respect to a time from an occurrence of an event. The event may include one or more of a time from an onset of the disease, a time from an onset of complications associated with the disease, and a time from an initiation of treatment associated with the disease.

In one embodiment, extracting imaging features from the input medical imaging data includes extracting a percent of opacity metric representing a total percent volume of lungs affected by the disease from the input medical imaging data.

In one embodiment, predicting risk for a medical event associated with evaluating or treating the patient for the disease includes predicting risk for a course of action for evaluating or treating the patient or predicting risk for a resource utilization for evaluating or treating the patient.

These and other advantages of the invention will be apparent to those of ordinary skill in the art by reference to the following detailed description and the accompanying drawings.

DETAILED DESCRIPTION

The present invention generally relates to methods and systems for risk prediction for COVID-19 (coronavirus disease 2019) patient management. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

COVID-19 is an infectious disease that typically presents a wide range of symptoms, ranging from asymptomatic to mild, moderate, severe, and critical symptoms. Over the course of COVID-19, patients may experience waves of improvement and deterioration over a time period of two weeks or more. During this time period, patient conditions can change dramatically (e.g., within hours) and may require emergency measures, such as, e.g., tracheal intubation for mechanical ventilation. Such emergency measures involve risk to both the patient (e.g., health risks) and to the caregivers (e.g., risk of infection). Given the novel nature of COVID-19 and its exponential spread, there is a lack of data and established protocols and workflows for patient management of patients suspected of, or confirmed as, having COVID-19.

Embodiments described herein provide for comprehensive risk prediction for patient management of patients suspected of, or confirmed as, having COVID-19 using one or more machine learning based systems. Embodiments described herein utilize medical imaging data of the patient, as well as other patient data, for risk prediction at various stages of patient management. Advantageously, embodiments described herein provide for comprehensive risk prediction for COVID-19 patient management to not only predict the risk associated with patient condition and treatment, but also the risk associated with operational and logistical measures (e.g., resource utilization of the hospital).

Figure 1:
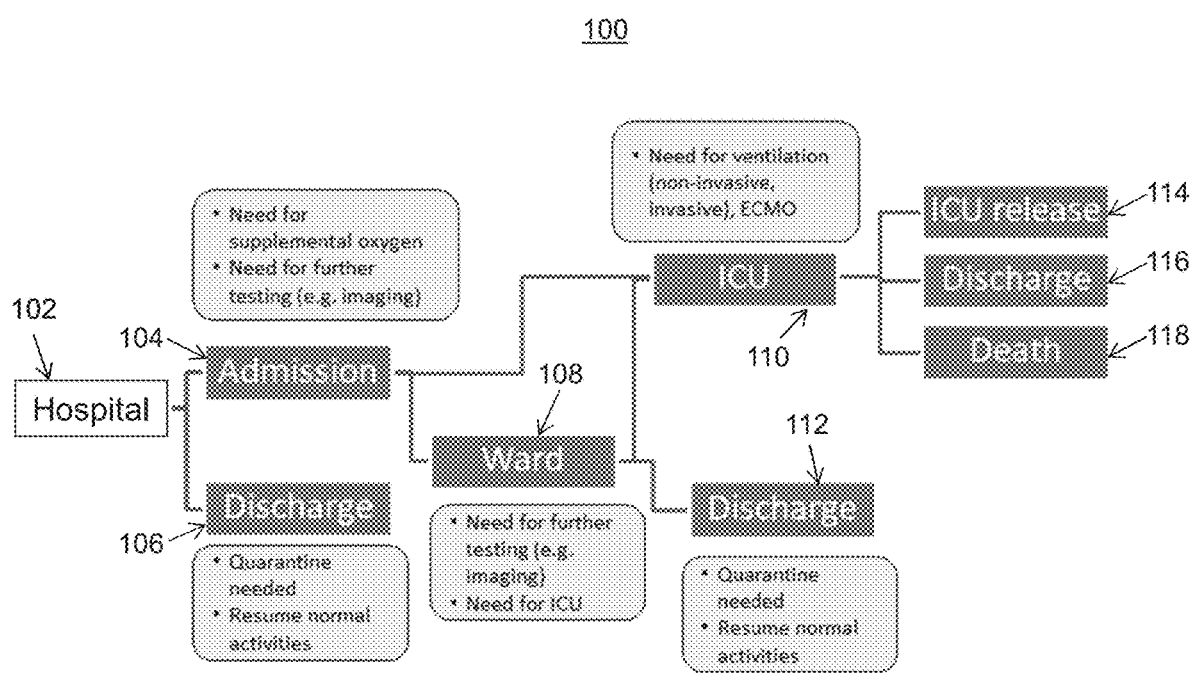
FIG. 1 shows an exemplary clinical workflow for a patient suspected of, or confirmed as, having COVID-19 (coronavirus disease 2019), in accordance with one or more embodiments.

FIG. 1 shows an exemplary clinical workflow 100 for a patient suspected of, or confirmed as, having COVID-19, in accordance with one or more embodiments. Possible predictions are shown in FIG. 1 at various stages of clinical workflow 100. Such predictions may be predicted in accordance with embodiments described herein.

As shown in FIG. 1, a patient arrives at a hospital or another clinical care setting (e.g., urgent care center, primary care office, telemedicine) (block 102), where the patient is either admitted (block 104) to the hospital or discharged (block 106) from the hospital. Where the patient is admitted (block 104), possible predictions include the need for supplemental oxygen or the need for further testing (e.g., imaging). Where the patient is discharged (block 106), possible predictions include whether quarantine is needed or whether the patient can resume normal activities. Once admitted, the patient may be placed in the ward (block 108) or the ICU (intensive care unit) 110. Where the patient is placed in the ward (block 108), possible predictions include the need for further testing (e.g., imaging) or the need for ICU. Once the patient is placed in the ward (block 108), the patient may be placed in the ICU (block 110) or discharged (block 112). Where the patient is placed in the ICU (block 110), possible predictions include the need for ventilation (non-invasive or invasive) or ECMO (extracorporeal membrane oxygenation). Where the patient is discharged (block 112), possible predictions include whether quarantine is needed or whether the patient can resume normal activities. Once the patient is placed in the ICU (block 110), the patient may be released from the ICU (block 114), discharged from the hospital (block 116), or die (block 118).

Figure 2:
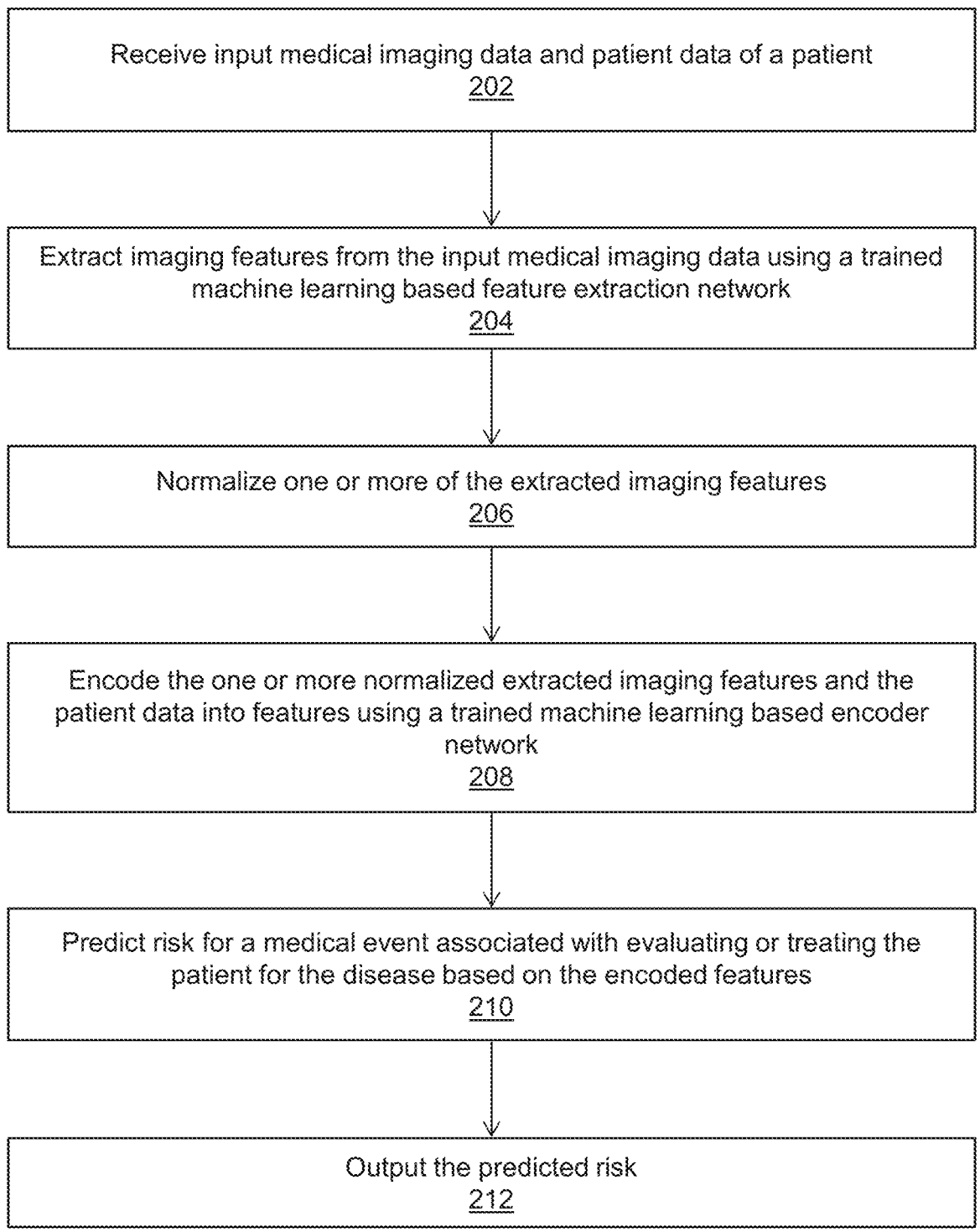
FIG. 2 shows a method for predicting risk for a medical event associated with evaluating or treating a patient for a disease, in accordance with one or more embodiments.

FIG. 2 shows a method 200 for predicting risk for a medical event associated with evaluating or treating a patient for a disease, in accordance with one or more embodiments. The steps of method 200 of FIG. 2 may be performed by one or more computing devices, such as, e.g., computer 702 of FIG. 7.

At step 202, input medical imaging data and patient data of the patient is received. The patient may be suspected of, or confirmed as, having a disease. In one embodiment, the disease is a member of the family of coronaviruses. In one embodiment, the disease is COVID-19. As used herein, COVID-19 includes mutations of the COVID-19 virus (which may be referred to by different terms). However, the disease may include any disease. For example, the disease may be other types of viral pneumonia (e.g., SARS (severe acute respiratory syndrome), MERS (Middle East respiratory syndrome), etc.), bacterial pneumonia, fungal pneumonia, mycoplasma pneumonia, or other types of pneumonia or other types of diseases.

In one embodiment, the input medical imaging data is of the chest (including the lungs and the heart) of the patient. However, the input medical imaging data may be of any anatomical structure or region of the patient. The input medical imaging data may depict radiographic abnormality patterns associated with the disease in the lungs of the patient. For example, where the disease is COVID-19, the abnormality patterns may include opacities such as, e.g., GGO (ground glass opacity), consolidation, crazy-paving pattern, atelectasis, interlobular septal thickening, pleural effusions, bronchiectasis, halo signs, etc.

In one embodiment, the input medical imaging data may include CT input medical imaging data or x-ray input medical imaging data. However, the input medical imaging data may be of any suitable modality, such as, e.g., MRI (magnetic resonance imaging), US (ultrasound), or any other modality or combination of modalities. The input medical imaging data may comprise 2D images or 3D volumes, and may comprise a single image or a plurality of images (e.g., a sequence of images acquired over time). The input medical imaging data may be received directly from an image acquisition device, such as, e.g., a CT or x-ray scanner, as the input medical imaging data is acquired, or can be received by loading previously acquired input medical imaging data from a storage or memory of a computer system or receiving the input medical imaging data from a remote computer system.

The patient data may include any data associated with the patient. The patient data may be retrieved from one or more medical databases associated with one or more clinical sites. Exemplary medical databases include EMRs (electronic medical records), EHRs (electronic health records), RIS' (radiological information systems), HIS (hospital information systems), PACS (picture archiving and communication systems), etc.

The patient data may include, for example, demographic information, examination results, symptoms, lab test results, comorbidities, treatments, and medical history for the patient. Demographic information may include, e.g., age, gender, race, and location and/or geographical features of the patient. Examination results may include, e.g., temperature, respiratory rate, blood pressure, heart rate, weight (obesity), current or former smoker, oxygen saturation of the patient (in the examination room, under supplemental oxygen, or under ventilation), viral load (e.g., number of viral particles present), and test or diagnosis results of the patient. In one embodiment, the test results include COVID-19 antibody test results. Symptoms may include, e.g., shortness of breath, temperature, cough, and muscle pain experienced by the patient. Lab tests results may include, e.g., RT-PCR (reverse transcription polymerase chain reactions) for COVID-19, tests for other viral respiratory infections diseases (e.g., rule out objective), blood cultures to confirm or rule out secondary bacterial infection, complete blood count including lymphocyte count, biomarkers such as creatinine, ferritin, C-reactive protein, procalcitonin, D-dimer, inflammatory cytokines, interleukins, etc., and troponin. Comorbidities may include, e.g., diabetes, hypertension, heart disease, kidney disease, chronic dialysis, cancer, asthma, chronic obstructive pulmonary disease, etc. Treatments may include, e.g., anti-viral therapies, antibiotics, anti-inflammatory therapies, respiratory therapy (including mechanical ventilation characteristics), ECMO treatment, and may include the start date relative to the onset of illness, the dose, and the length). Medical history may include, e.g., prior tests, prior examinations, prior diagnoses, prior treatments, and family history.

In one embodiment, the patient data may include an identification of organs or systems affected by the disease. In one example, the organs or systems include the lungs. COVID-19 is a respiratory disease that typically presents with cough, shortness of breath, and pneumonia. In another example, the organs or systems include the heart and cardiovascular system. COVID-19 patients with underlying cardiovascular conditions are at a higher risk and generally have worse outcomes (including death). Additionally, cardiac injury (e.g., myocarditis, arrhythmias) has been noted in COVID-19 patients and many anti-viral therapies have side effects involving the cardiovascular system. In another example, the organs or systems include thromboembolic complications. Pulmonary embolisms and deep-vein thrombosis may occur in patients with COVID-19 and require careful selection and monitoring of anticoagulation therapy. In another example, the organs or systems includes the kidney (e.g., for kidney failure).

At step 204, imaging features are extracted from the input medical imaging data. In one embodiment, the imaging features may be automatically extracted from the input medical imaging data using a trained machine learning based feature extraction network. However, the imaging features may additionally or alternatively be manually extracted from the input medical imaging data by a radiologist or any other user (as a radiology report). In one embodiment, the imaging features may be automatically extracted from the imaging data using a trained machine learning based system in accordance with known techniques.

Figure 3:
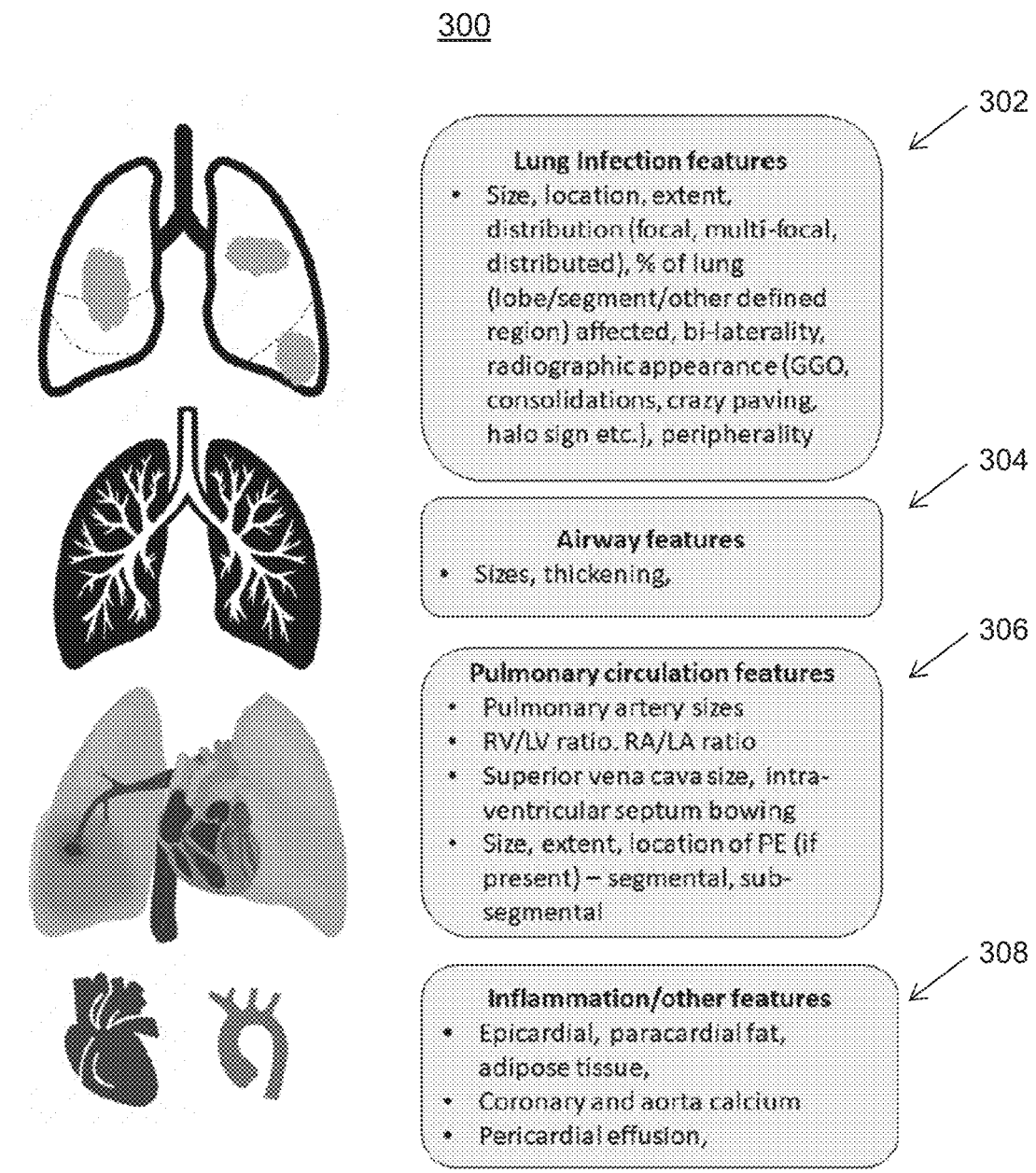
FIG. 3 shows various imaging features that may be extracted from input medical imaging data of a patient, in accordance with one or more embodiments.

FIG. 3 shows various imaging features 300 that may be extracted from input medical imaging data of a patient, in accordance with one or more embodiments. Imaging features 300 shown in FIG. 3 may be the imaging features extracted at step 204 of method 200 of FIG. 2. Imaging features 300 may be automatically extracted from imaging data using a trained machine learning based system or manually extracted from the imaging data by a radiologist. Imaging features 300 include lung infection features 302, airway features 304, pulmonary circulation features 306, and inflammation or other features 308.

Lung infection features 302 include, e.g., the presence of airspace abnormality patterns (e.g., opacities), the size of the abnormality patterns, the location of the abnormality patterns, the extent of the abnormality patterns, the distribution of the abnormality patterns (e.g., focal, multi-focal, or distributed; central or peripheral, bi-lateral, etc.), the percentage of lung (e.g., lobe, segment, or other defined region of the lung) affected by the abnormality patterns (e.g., a POO (percent of opacity) metric representing the total percent volume of the lungs affected by the disease or a LSS (lung severity score) metric representing a cumulative measure of the extent of lung involvement in the disease across each lobe of the lungs), and the radiographic appearance of the abnormality patterns (e.g., GGO, consolidation, crazy-paving pattern, atelectasis, interlobular septal thickening, pleural effusions, bronchiectasis, halo signs, etc.). In one embodiment, lung infection features 302 includes a comparison of histograms of the abnormality patterns (in the entire lungs, in particular lobes, or in any other specific region of the lungs) at two or more time points. For example, a KL (Kullback-Leibler) divergence may be determined to compare histograms of abnormality patterns.

Airway features 304 include, e.g., the size, the thickening, and the distribution of the airways of the lungs of the patient.

Pulmonary circulation features 306 include, e.g., pulmonary artery sizes, the right ventricular-to-left ventricular (RV/LV) diameter ratio, the right atrial-to-left atrial (RA/LA) area ratio, the superior vena cava size, the intraventricular septum bowing, and the size, extent, location (segmental, sub-segmental), and total clot burden of any pulmonary embolisms.

The inflammation and other features 308 include, e.g., epicardial, paracardial fat, and adipose tissue, coronary and aortic calcium, pericardial effusion, emphysema (low attenuation in airspaces), supra-aortic calcium, carotids, etc.

In one embodiment, imaging features 300 include the rate of change of the lung infection features 302, airway features 304, pulmonary circulation features 306, and inflammation or other features 308 over time.

At step 206, one or more of the extracted imaging features are normalized. Normalization of the one or more extracted imaging features adjusts the values of the extracted imaging features to a standard scale.

In one embodiment, the one or more extracted imaging features are normalized with respect to other ones of the extracted imaging features. For example, the percentage of the lung affected by opacities may be normalized with respect to the pulmonary embolism size by dividing the percentage of the lung affected by opacities by the pulmonary embolism size. In another embodiment, the total lung volume may be normalized with respect to the size of the abnormality patterns. In one embodiment, the one or more extracted imaging features may be normalized with respect to other ones of the extracted imaging features associated with other organs or systems.

In one embodiment, the one or more extracted imaging features are temporally normalized with respect to a time from the occurrence of a medical event. For example, one or more extracted imaging features may be normalized with respect to the time from the onset of the disease, such as, e.g., the time from the patient experiencing a cough and a fever, which are typical day 1 symptoms representing the onset of COVID-19. For example, the size of the abnormality pattern may be divided by the number of days from the onset of COVID-19. In another example, the one or more extracted imaging features may be normalized with respect to the time from the onset of complications associated with the disease, such as, e.g., the onset of dyspnea (shortness of breath, which is a typical day 7 symptom of COVID-19), the onset of hypoxia (reduced oxygen saturation, which may be with the patient in the hospital room or under supplemental oxygen), the onset of major complications (e.g., multi-organ failure or septic shock). In another example, the one or more extracted imaging features may be normalized with respect to the time from the initiation of treatment associated with disease, such as, e.g., the start of anti-viral therapy, anti-inflammatory therapy, mechanical ventilation, or ECMO. Other medical events are also contemplated, such as, e.g., admission to the intensive care unit or a particular viral load (the number of viral particles present).

In one embodiment, the one or more extracted imaging features are normalized with respect to a plurality of patients.

In one embodiment, the extracting imaging features are normalized by modulating the weights of the encoder network utilized at step 208.

At step 208, the one or more normalized extracted imaging features and the patient data are encoded into features using a trained machine learning based encoder network. In one embodiment, the input medical imaging data may also be encoded into the features by the encoder network. The encoded features are low dimensional features in the latent space that has a size substantially less than the size of the data input into the encoder network (i.e., the normalized extract imaging features, the patient data, and possibly the input medical imaging data). The encoder network is trained, together with a decoder network, during a prior offline or training stage. Once trained, the encoder network is applied at step 208 during an online or inference stage. The training of the encoder network is further described below with respect to FIG. 4.

At step 210, risk for a medical event associated with evaluating or treating the patient for the disease is predicted based on the encoded features. In one embodiment, the risk is predicted using a trained machine learning risk prediction network. The risk prediction network is trained to map features to a predicted risk for a particular medical event during a prior offline or training stage. Once trained, the risk prediction network is applied at step 210 during an online or inference stage. The training of the risk prediction network is further described below with respect to FIG. 4.

The risk prediction network may be trained or retrained for any medical event associated with evaluating or treating the patient for patient management. In one embodiment, the medical event includes a course of action for evaluating or treating the patient. For example, the course of action may be admission or discharge from the hospital, quarantine or resumption of normal activities, transfer to intensive care unit, testing, therapy (e.g., supplemental oxygen, ventilation (invasive, non-invasive, or long term ventilation requiring tracheotomy), anti-viral therapy (including compassionate use therapy where there is a lack of established efficacy or risk of severe side effects), anti-inflammatory therapy, ECMO treatment (if mechanical ventilation is insufficient). In one embodiment, the medical event includes a medical condition of the patient. For example, the medical condition may be the predicted medical condition of the patient after applying a course of action. In one embodiment, the medical event includes operational metrics or resource utilization for evaluating or treating the patient. For example, the resource utilization may be the length of stay at the hospital or intensive care unit, the likelihood of readmission to the hospital, the number of nurses, doctors, or other medical staff, and medical resource usage.

In one embodiment, the risk prediction network may be adapted based on geographic region (e.g., by country, state, or county) to account for different patient populations or based on a time relative to a medical event associated with the disease (e.g., a relative time in the COVID-19 pandemic) to account for varying symptoms.

In one embodiment, the risk prediction network may be a LSTM (long short-term memory) based network to learn the temporal changes in the distribution of the abnormality pattern from training data (with timestamps) during the training stage and apply the temporal changes at step 210 during the inference stage.

At step 212, the predicted risk is output. For example, the predicted risk can be output by displaying the predicted risk on a display device of a computer system, storing the predicted risk on a memory or storage of a computer system, or by transmitting the predicted risk to a remote computer system.

Figure 4:
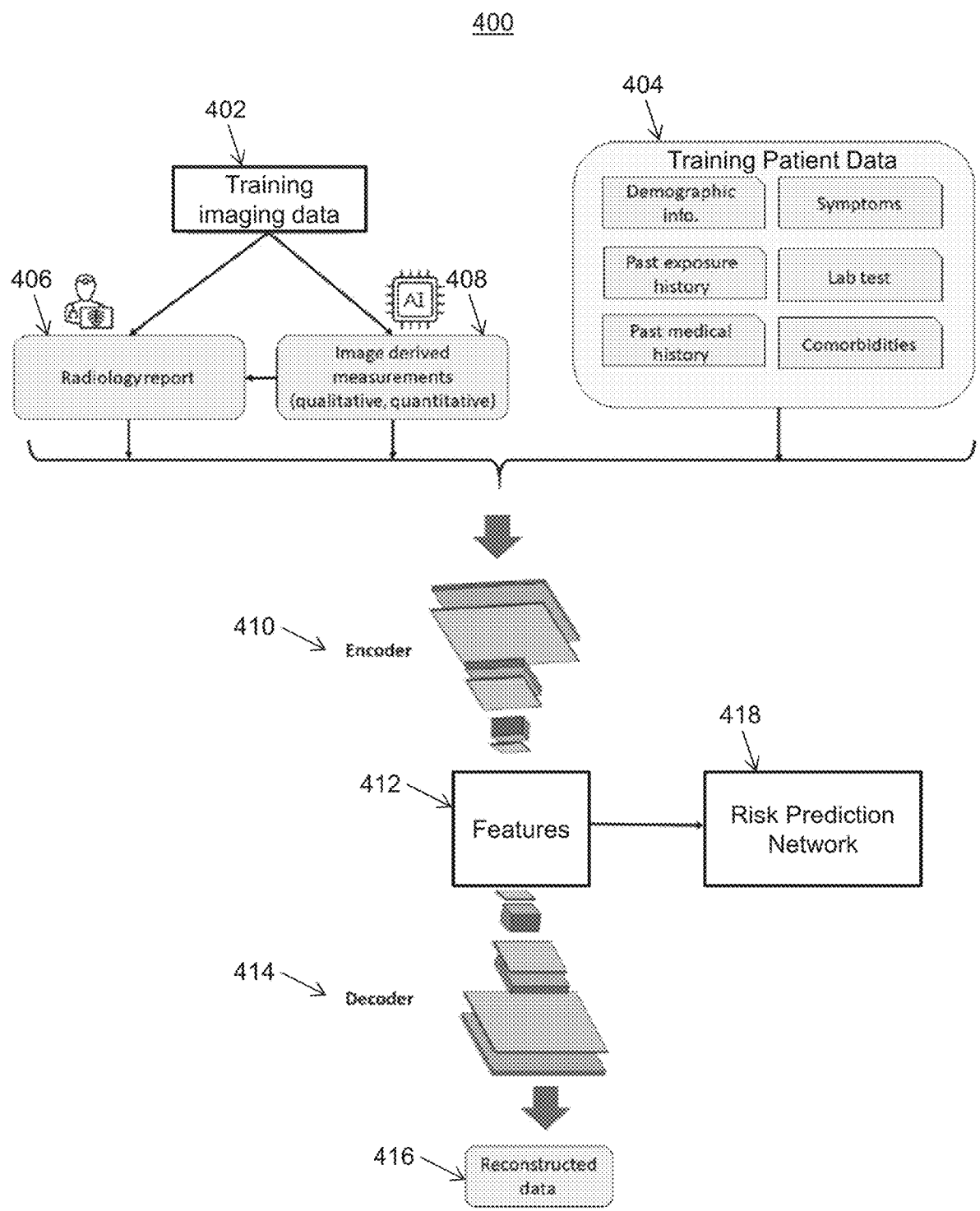
FIG. 4 shows a framework for training one or more machine learning based systems for predicting risk for a medical event associated with evaluating or treating a patient for a disease, in accordance with one or more embodiments.

FIG. 4 shows a framework 400 for training one or more machine learning based systems for predicting risk for a medical event associated with evaluating or treating a patient for a disease, in accordance with one or more embodiments. Framework 400 comprises an encoder network 410, a decoder network 414, and a risk prediction network 418. Encoder network 410, a decoder network 414, and a risk prediction network 418 are trained in accordance with framework 400 during an offline or training stage. Once trained, encoder network 410 and risk prediction network 418 are applied during an online or inference stage. In one embodiment, encoder network 410 is applied at step 208 of method 200 of FIG. 2 and risk prediction network 418 is applied at step 210 of method 200 of FIG. 2. Decoder network 414 is only utilized during the training stage in order to constrain and regularize encoder network 410, and is not applied during the inference stage.

Encoder network 410 and decoder network 414 are trained together and form an autoencoder. Encoder network 410 receives input training data comprising radiology report 406 and image derived measurements 408 (qualitative and quantitative measurements) extracted from training imaging data 402. Features from the radiology report 406 and image derived measurements 408 may be normalized. Input training data also comprises training patient data 404, which may include demographic information, symptoms, past exposure history, lab tests, past medical history, and comorbidities of the patient. In some embodiments, input training data also comprises training imaging data 402. Encoder network 410 comprises a plurality of layers that encode the input training data into low level features 412 in the latent space. Features 412 have a size that is substantially less than the size of the input training data. Decoder network 414 comprises a plurality of layers that recode features 412 to generate reconstructed data 416 representing a reconstruction of the training input data input into encoder network 410.

Risk prediction network 418 may be any machine learning based network (e.g., neural network or deep neural network). Risk prediction network 418 is trained using a training dataset to learn a mapping between features and a predicted risk for a medical event. The training dataset comprises features (e.g., features 412) with corresponding ground truth values. The ground truth values are labels identifying an expected result (for a particular medical event) for the corresponding features.

Encoder network 410/decoder network 414 and risk prediction network 418 may be individually trained or trained together in an end-to-end fashion.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, embodiments described herein are described with respect to methods and systems for risk prediction for COVID-19 patient management using a trained machine learning based generator network, as well as with respect to methods and systems for training a machine learning based generator network for risk prediction for COVID-19 patient management. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based network of the methods and systems for risk prediction for COVID-19 patient management can be adapted by the methods and systems for training the machine learning based generator network for risk prediction for COVID-19 patient management. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 5:
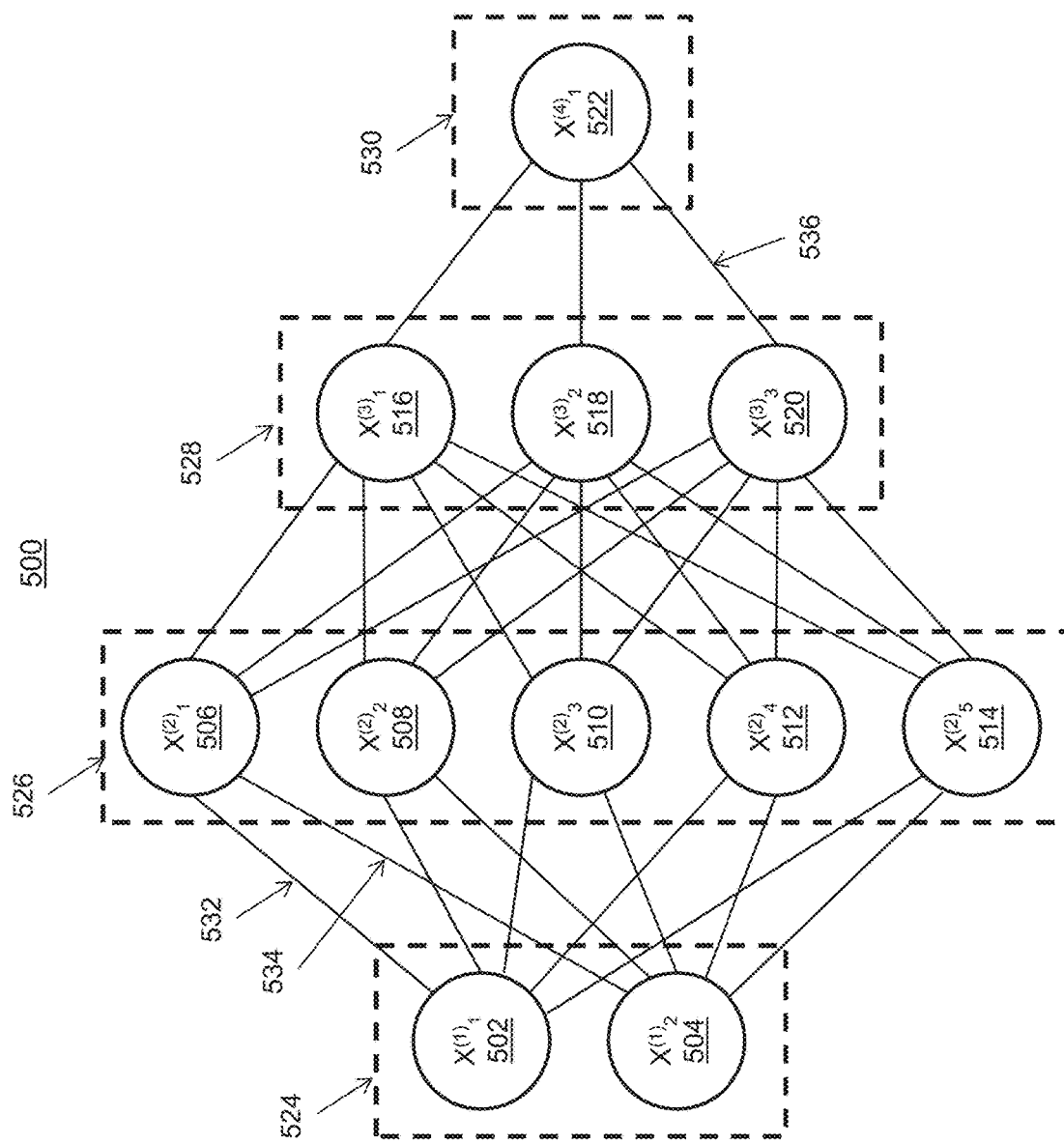
FIG. 5 shows an exemplary artificial neural network that may be used to implement one or more embodiments described herein.

FIG. 5 shows an embodiment of an artificial neural network 500, in accordance with one or more embodiments. Alternative terms for "artificial neural network" are "neural network", "artificial neural net" or "neural net". Machine learning networks described herein, such as, e.g., the machine learning based system applied at step 204 of FIG. 2, the machine learning based encoder network applied at step 208 of FIG. 2, the risk prediction network applied at step 210 of FIG. 2, and encoder network 410, decoder network 414, and risk prediction network 418 of FIG. 4, may be implemented using artificial neural network 500.

The artificial neural network 500 comprises nodes 502-522 and edges 532, 534, . . . , 536, wherein each edge 532, 534, . . . , 536 is a directed connection from a first node 502-522 to a second node 502-522. In general, the first node 502-522 and the second node 502-522 are different nodes 502-522, it is also possible that the first node 502-522 and the second node 502-522 are identical. For example, in FIG. 5, the edge 532 is a directed connection from the node 502 to the node 506, and the edge 534 is a directed connection from the node 504 to the node 506. An edge 532, 534, . . . , 536 from a first node 502-522 to a second node 502-522 is also denoted as "ingoing edge" for the second node 502-522 and as "outgoing edge" for the first node 502-522.

In this embodiment, the nodes 502-522 of the artificial neural network 500 can be arranged in layers 524-530, wherein the layers can comprise an intrinsic order introduced by the edges 532, 534, . . . , 536 between the nodes 502-522. In particular, edges 532, 534, . . . , 536 can exist only between neighboring layers of nodes. In the embodiment shown in FIG. 5, there is an input layer 524 comprising only nodes 502 and 504 without an incoming edge, an output layer 530 comprising only node 522 without outgoing edges, and hidden layers 526, 528 in-between the input layer 524 and the output layer 530. In general, the number of hidden layers 526, 528 can be chosen arbitrarily. The number of nodes 502 and 504 within the input layer 524 usually relates to the number of input values of the neural network 500, and the number of nodes 522 within the output layer 530 usually relates to the number of output values of the neural network 500.

In particular, a (real) number can be assigned as a value to every node 502-522 of the neural network 500. Here, $x^{(n)}_i$ denotes the value of the i-th node 502-522 of the n-th layer 524-530. The values of the nodes 502-522 of the input layer 524 are equivalent to the input values of the neural network 500, the value of the node 522 of the output layer 530 is equivalent to the output value of the neural network 500. Furthermore, each edge 532, 534, . . . , 536 can comprise a weight being a real number, in particular, the weight is a real number within the interval [−1, 1] or within the interval [0, 1]. Here, $w^{(m,n)}_{i,j}$ the weight of the edge between the i-th node 502-522 of the m-th layer 524-530 and the j-th node 502-522 of the n-th layer 524-530. Furthermore, the abbreviation $w^{(n)}_{i,j}$ is defined for the weight $w^{(n,n+1)}_{i,j}$.

In particular, to calculate the output values of the neural network 500, the input values are propagated through the neural network. In particular, the values of the nodes 502-522 of the (n+1)-th layer 524-530 can be calculated based on the values of the nodes 502-522 of the n-th layer 524-530 by $$x_j^{(n+1)}=f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions The transfer function is mainly used for normalization purposes.

In particular, the values are propagated layer-wise through the neural network, wherein values of the input layer 524 are given by the input of the neural network 500, wherein values of the first hidden layer 526 can be calculated based on the values of the input layer 524 of the neural network, wherein values of the second hidden layer 528 can be calculated based in the values of the first hidden layer 526, etc.

In order to set the values $w^{(m,n)}_{i,j}$ for the edges, the neural network 500 has to be trained using training data. In particular, training data comprises training input data and training output data (denoted as $t_i$). For a training step, the neural network 500 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 500 (backpropagation algorithm). In particular, the weights are changed according to $$w'^{(n)}_{i,j}=w^{(n)}_{i,j}-\gamma \cdot \delta_j^{(n)} \cdot x_i^{(n)}$$

wherein γ is a learning rate, and the numbers $\delta^{(n)}_j$ can be recursively calculated as $$\delta^{(n)}_j = (\Sigma_k \delta^{(n+1)}_k \cdot w^{(n+1)}_{j,k}) \cdot f'(\Sigma_i x^{(n)}_i \cdot w^{(n)}_{i,j})$$

based on $\delta^{(n+1)}_j$, if the (n+1)-th layer is not the output layer, and $$\delta^{(n)}_j = (x^{(n+1)}_k - t^{(n+1)}_j) \cdot f'(\Sigma_i x^{(n)}_i \cdot w^{(n)}_{i,j})$$

if the (n+1)-th layer is the output layer 530, wherein f' is the first derivative of the activation function, and $y^{(n+1)}_j$ is the comparison training value for the j-th node of the output layer 530.

Figure 6:
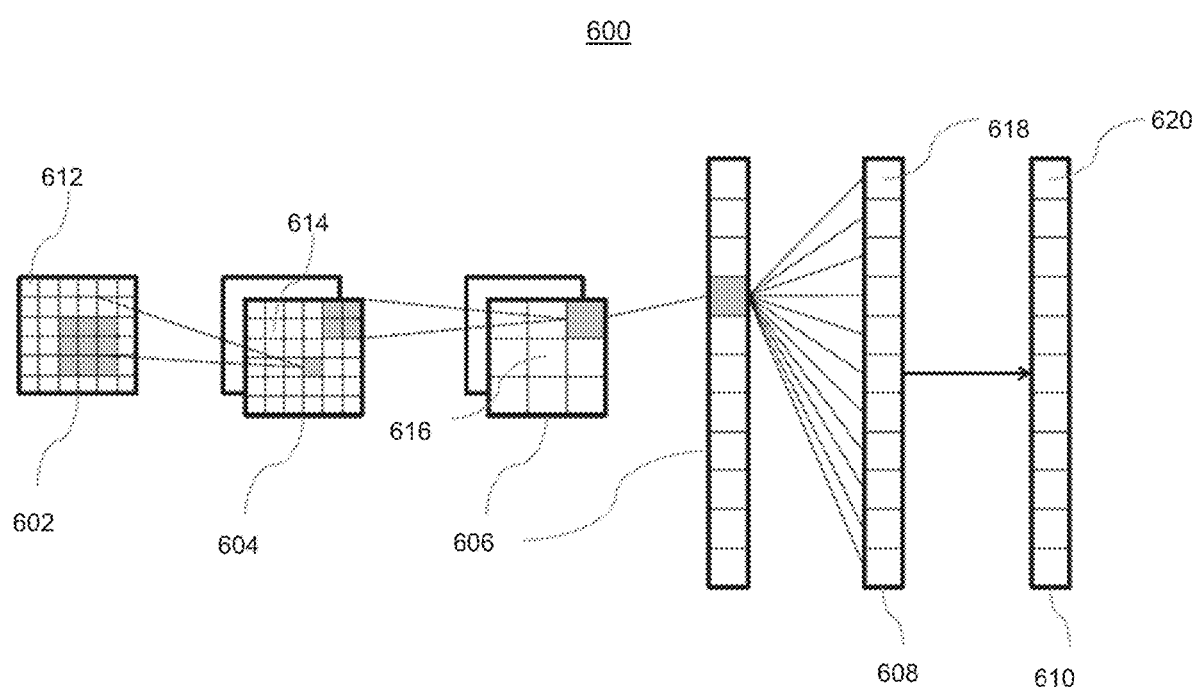
FIG. 6 shows a convolutional neural network that may be used to implement one or more embodiments described herein.

FIG. 6 shows a convolutional neural network 600, in accordance with one or more embodiments. Machine learning networks described herein, such as, e.g., the machine learning based system applied at step 204 of FIG. 2, the machine learning based encoder network applied at step 208 of FIG. 2, the risk prediction network applied at step 210 of FIG. 2, and encoder network 410, decoder network 414, and risk prediction network 418 of FIG. 4, may be implemented using convolutional neural network 600.

In the embodiment shown in FIG. 6, the convolutional neural network comprises 600 an input layer 602, a convolutional layer 604, a pooling layer 606, a fully connected layer 608, and an output layer 610. Alternatively, the convolutional neural network 600 can comprise several convolutional layers 604, several pooling layers 606, and several fully connected layers 608, as well as other types of layers. The order of the layers can be chosen arbitrarily, usually fully connected layers 608 are used as the last layers before the output layer 610.

In particular, within a convolutional neural network 600, the nodes 612-620 of one layer 602-610 can be considered to be arranged as a d-dimensional matrix or as a d-dimensional image. In particular, in the two-dimensional case the value of the node 612-620 indexed with i and j in the n-th layer 602-610 can be denoted as $x^{(n)}_{[i,j]}$. However, the arrangement of the nodes 612-620 of one layer 602-610 does not have an effect on the calculations executed within the convolutional neural network 600 as such, since these are given solely by the structure and the weights of the edges.

In particular, a convolutional layer 604 is characterized by the structure and the weights of the incoming edges forming a convolution operation based on a certain number of kernels. In particular, the structure and the weights of the incoming edges are chosen such that the values $x^{(n)}_k$ of the nodes 614 of the convolutional layer 604 are calculated as a convolution $x^{(n)}_k = K_k * x^{(n-1)}$ based on the values $x^{(n-1)}$ of the nodes 612 of the preceding layer 602, where the convolution * is defined in the two-dimensional case as $$x^{(n)}_k[i,j] = (K_k * x^{(n-1)})[i,j] \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 612-618 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 612-620 in the respective layer 602-610. In particular, for a convolutional layer 604, the number of nodes 614 in the convolutional layer is equivalent to the number of nodes 612 in the preceding layer 602 multiplied with the number of kernels.

If the nodes 612 of the preceding layer 602 are arranged as a d-dimensional matrix, using a plurality of kernels can be interpreted as adding a further dimension (denoted as "depth" dimension), so that the nodes 614 of the convolutional layer 614 are arranged as a (d+1)-dimensional matrix. If the nodes 612 of the preceding layer 602 are already arranged as a (d+1)-dimensional matrix comprising a depth dimension, using a plurality of kernels can be interpreted as expanding along the depth dimension, so that the nodes 614 of the convolutional layer 604 are arranged also as a (d+1)-dimensional matrix, wherein the size of the (d+1)-dimensional matrix with respect to the depth dimension is by a factor of the number of kernels larger than in the preceding layer 602.

The advantage of using convolutional layers 604 is that spatially local correlation of the input data can exploited by enforcing a local connectivity pattern between nodes of adjacent layers, in particular by each node being connected to only a small region of the nodes of the preceding layer.

In embodiment shown in FIG. 6, the input layer 602 comprises 36 nodes 612, arranged as a two-dimensional 6×6 matrix. The convolutional layer 604 comprises 72 nodes 614, arranged as two two-dimensional 6×6 matrices, each of the two matrices being the result of a convolution of the values of the input layer with a kernel. Equivalently, the nodes 614 of the convolutional layer 604 can be interpreted as arranges as a three-dimensional 6×6×2 matrix, wherein the last dimension is the depth dimension.

A pooling layer 606 can be characterized by the structure and the weights of the incoming edges and the activation function of its nodes 616 forming a pooling operation based on a non-linear pooling function f. For example, in the two dimensional case the values $x^{(n)}$ of the nodes 616 of the pooling layer 606 can be calculated based on the values $x^{(n-1)}$ of the nodes 614 of the preceding layer 604 as $$x^{(n)}[i,j] = f(x^{(n-1)}[id_1, jd_2], \ldots, x^{(n-1)}[id_1 + d_1 - 1, jd_2 - d_2 - 1])$$

In other words, by using a pooling layer 606, the number of nodes 614, 616 can be reduced, by replacing a number d1·d2 of neighboring nodes 614 in the preceding layer 604 with a single node 616 being calculated as a function of the values of said number of neighboring nodes in the pooling layer. In particular, the pooling function f can be the max-function, the average or the L2-Norm. In particular, for a pooling layer 606 the weights of the incoming edges are fixed and are not modified by training.

The advantage of using a pooling layer 606 is that the number of nodes 614, 616 and the number of parameters is reduced. This leads to the amount of computation in the network being reduced and to a control of overfitting.

In the embodiment shown in FIG. 6, the pooling layer 606 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 608 can be characterized by the fact that a majority, in particular, all edges between nodes 616 of the previous layer 606 and the nodes 618 of the fully-connected layer 608 are present, and wherein the weight of each of the edges can be adjusted individually.

In this embodiment, the nodes 616 of the preceding layer 606 of the fully-connected layer 608 are displayed both as two-dimensional matrices, and additionally as non-related nodes (indicated as a line of nodes, wherein the number of nodes was reduced for a better presentability). In this embodiment, the number of nodes 618 in the fully connected layer 608 is equal to the number of nodes 616 in the preceding layer 606. Alternatively, the number of nodes 616, 618 can differ.

Furthermore, in this embodiment, the values of the nodes 620 of the output layer 610 are determined by applying the Softmax function onto the values of the nodes 618 of the preceding layer 608. By applying the Softmax function, the sum the values of all nodes 620 of the output layer 610 is 1, and all values of all nodes 620 of the output layer are real numbers between 0 and 1.

A convolutional neural network 600 can also comprise a ReLU (rectified linear units) layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are $f(x)=\max(0,x)$, the tangent hyperbolics function or the sigmoid function.

In particular, convolutional neural networks 600 can be trained based on the backpropagation algorithm. For preventing overfitting, methods of regularization can be used, e.g. dropout of nodes 612-620, stochastic pooling, use of artificial data, weight decay based on the L1 or the L2 norm, or max norm constraints.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 2. Certain steps or functions of the methods and workflows described herein, including one or more of the steps or functions of FIG. 2, may be performed by a server or by another processor in a network-based cloud-computing system. Certain steps or functions of the methods and workflows described herein, including one or more of the steps of FIG. 2, may be performed by a client computer in a network-based cloud computing system. The steps or functions of the methods and workflows described herein, including one or more of the steps of FIG. 2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 7:
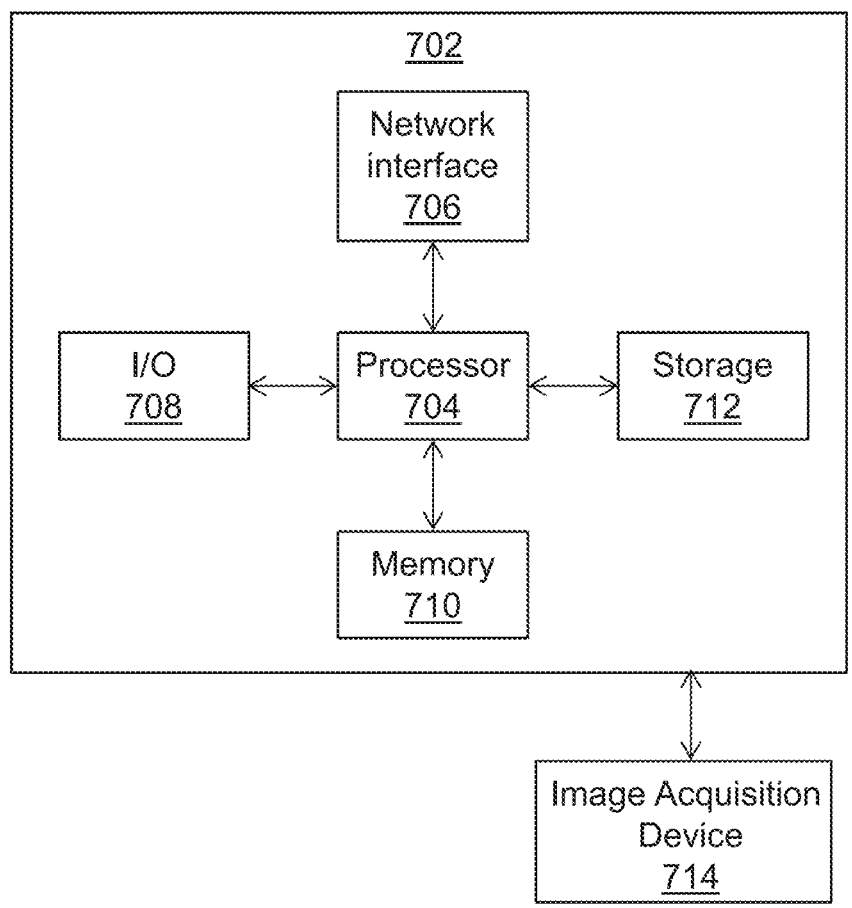
FIG. 7 shows a high-level block diagram of a computer that may be used to implement one or more embodiments described herein.

A high-level block diagram of an example computer 702 that may be used to implement systems, apparatus, and methods described herein is depicted in FIG. 7. Computer 702 includes a processor 704 operatively coupled to a data storage device 712 and a memory 710. Processor 704 controls the overall operation of computer 702 by executing computer program instructions that define such operations. The computer program instructions may be stored in data storage device 712, or other computer readable medium, and loaded into memory 710 when execution of the computer program instructions is desired. Thus, the method and workflow steps or functions of FIG. 2 can be defined by the computer program instructions stored in memory 710 and/or data storage device 712 and controlled by processor 704 executing the computer program instructions. For example, the computer program instructions can be implemented as computer executable code programmed by one skilled in the art to perform the method and workflow steps or functions of FIG. 2. Accordingly, by executing the computer program instructions, the processor 704 executes the method and workflow steps or functions of FIG. 2. Computer 702 may also include one or more network interfaces 706 for communicating with other devices via a network. Computer 702 may also include one or more input/output devices 708 that enable user interaction with computer 702 (e.g., display, keyboard, mouse, speakers, buttons, etc.).

Processor 704 may include both general and special purpose microprocessors, and may be the sole processor or one of multiple processors of computer 702. Processor 704 may include one or more central processing units (CPUs), for example. Processor 704, data storage device 712, and/or memory 710 may include, be supplemented by, or incorporated in, one or more application-specific integrated circuits (ASICs) and/or one or more field programmable gate arrays (FPGAs).

Data storage device 712 and memory 710 each include a tangible non-transitory computer readable storage medium. Data storage device 712, and memory 710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 708 may include peripherals, such as a printer, scanner, display screen, etc. For example, input/output devices 708 may include a display device such as a cathode ray tube (CRT) or liquid crystal display (LCD) monitor for displaying information to the user, a keyboard, and a pointing device such as a mouse or a trackball by which the user can provide input to computer 702.

An image acquisition device 714 can be connected to the computer 702 to input image data (e.g., medical images) to the computer 702. It is possible to implement the image acquisition device 714 and the computer 702 as one device. It is also possible that the image acquisition device 714 and the computer 702 communicate wirelessly through a network. In a possible embodiment, the computer 702 can be located remotely with respect to the image acquisition device 714.

Any or all of the systems and apparatus discussed herein, including the machine learning based system applied at step 204 of FIG. 2, the machine learning based encoder network applied at step 208 of FIG. 2, the risk prediction network applied at step 210 of FIG. 2, the encoder network 410, decoder network 414, and risk prediction network 418 of FIG. 4, the artificial neural network 500 of FIG. 5, and the convolutional neural network 600 of FIG. 6, may be implemented using one or more computers such as computer 702.

One skilled in the art will recognize that an implementation of an actual computer or computer system may have other structures and may contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer implemented method comprising:
receiving input medical imaging data and patient data of a patient, the input medical imaging data comprising abnormality patterns associated with a disease;
extracting imaging features from the input medical imaging data;
temporally normalizing the extracted imaging features by dividing the extracted imaging features by a time from an occurrence of a particular medical event;
encoding the normalized extracted imaging features and the patient data into encoded features; and
predicting risk for an event associated with evaluating or treating the patient for the disease based on the encoded features using a trained machine learning based risk prediction network, wherein the trained machine leaning based risk prediction network is trained based on 1) features encoded from training imaging data and training patient data and 2) corresponding ground truth values identifying an expected result for the features.

2. The computer implemented method of claim 1, wherein the disease is COVID-19 (coronavirus disease 2019) and the abnormality patterns comprise at least one of GGO (ground glass opacity), consolidation, and crazy-paving pattern.

3. The computer implemented method of claim 1, wherein temporally normalizing the extracted imaging features by dividing the extracted imaging features by a time from an occurrence of a particular medical event comprises:
dividing the extracted imaging features by a time from an onset of the disease.

4. The computer implemented method of claim 1, wherein extracting imaging features from the input medical imaging data comprises:
extracting a percent of opacity metric representing a total percent volume of lungs affected by the disease from the input medical imaging data.

5. The computer implemented method of claim 1, wherein predicting risk for an event associated with evaluating or treating the patient for the disease based on the encoded features using a trained machine learning based risk prediction network comprises:
predicting risk for a course of action for evaluating or treating the patient.

6. The computer implemented method of claim 1, wherein predicting risk for an event associated with evaluating or treating the patient for the disease based on the encoded features using a trained machine learning based risk prediction network comprises:
predicting risk for a resource utilization for evaluating or treating the patient.

7. The computer implemented method of claim 1, wherein the disease is a pneumonia.

8. An apparatus comprising:
means for receiving input medical imaging data and patient data of a patient, the input medical imaging data comprising abnormality patterns associated with a disease;
means for extracting imaging features from the input medical imaging data;
means for temporally normalizing the extracted imaging features by dividing the extracted imaging features by a time from an occurrence of a particular medical event;
means for encoding the normalized extracted imaging features and the patient data into encoded features; and
means for predicting risk for an event associated with evaluating or treating the patient for the disease based on the encoded features using a trained machine learning based risk prediction network, wherein the trained machine leaning based risk prediction network is trained based on 1) features encoded from training imaging data and training patient data and 2) corresponding ground truth values identifying an expected result for the features.

9. The apparatus of claim 8, wherein the disease is COVID-19 (coronavirus disease 2019) and the abnormality patterns comprise at least one of GGO (ground glass opacity), consolidation, and crazy-paving pattern.

10. The apparatus of claim 8, wherein the means for temporally normalizing the extracted imaging features by dividing the extracted imaging features by a time from an occurrence of a particular medical event comprises:
   means for dividing the extracted imaging features by a time from an onset of the disease.

11. A non-transitory computer readable medium storing computer program instructions, the computer program instructions when executed by a processor cause the processor to perform operations comprising:
   receiving input medical imaging data and patient data of a patient, the input medical imaging data comprising abnormality patterns associated with a disease;
   extracting imaging features from the input medical imaging data;
   temporally normalizing the extracted imaging features by dividing the extracted imaging features by a time from an occurrence of a particular medical event;
   encoding the normalized extracted imaging features and the patient data into encoded features; and
   predicting risk for an event associated with evaluating or treating the patient for the disease based on the encoded features using a trained machine learning based risk prediction network, wherein the trained machine leaning based risk prediction network is trained based on 1) features encoded from training imaging data and training patient data and 2) corresponding ground truth values identifying an expected result for the features.

12. The non-transitory computer readable medium of claim 11, wherein the disease is COVID-19 (coronavirus disease 2019) and the abnormality patterns comprise at least one of GGO (ground glass opacity), consolidation, and crazy-paving pattern.

13. The non-transitory computer readable medium of claim 11, wherein extracting imaging features from the input medical imaging data comprises:
   extracting a percent of opacity metric representing a total percent volume of lungs affected by the disease from the input medical imaging data.

14. The non-transitory computer readable medium of claim 11, wherein predicting risk for an event associated with evaluating or treating the patient for the disease based on the encoded features using a trained machine learning based risk prediction network comprises:
   predicting risk for a course of action for evaluating or treating the patient.

15. The non-transitory computer readable medium of claim 11, wherein predicting risk for an event associated with evaluating or treating the patient for the disease based on the encoded features using a trained machine learning based risk prediction network comprises:
   predicting risk for a resource utilization for evaluating or treating the patient.

16. The non-transitory computer readable medium of claim 11, wherein the disease is a pneumonia.

17. The computer implemented method of claim 1, wherein temporally normalizing the extracted imaging features by dividing the extracted imaging features by a time from an occurrence of a particular medical event comprises:
   dividing the extracted imaging features by a time from an onset of complications associated with the disease.

18. The computer implemented method of claim 1, wherein temporally normalizing the extracted imaging features by dividing the extracted imaging features by a time from an occurrence of a particular medical event comprises:
   dividing the extracted imaging features by a time from an initiation of treatment associated with the disease.

19. The apparatus of claim 8, wherein the means for temporally normalizing the extracted imaging features by dividing the extracted imaging features by a time from an occurrence of a particular medical event comprises:
   means for dividing the extracted imaging features by a time from an onset of complications associated with the disease.

20. The non-transitory computer readable medium of claim 11, wherein temporally normalizing the extracted imaging features by dividing the extracted imaging features by a time from an occurrence of a particular medical event comprises:
   dividing the extracted imaging features by a time from an initiation of treatment associated with the disease.

* * * * *